United States Patent [19]

Staudinger et al.

[11] Patent Number: 4,775,991
[45] Date of Patent: Oct. 4, 1988

[54] METHOD OF AND APPARATUS FOR GRAIN-SIZE ANALYSIS

[75] Inventors: Gernot Staudinger, Messendorfberg 99, A8042 Graz; Peter Pechtl; Manfred Hangl, both of Graz, all of Austria

[73] Assignee: Gernot Staudinger, Graz, Austria

[21] Appl. No.: 870,635

[22] Filed: Jun. 4, 1986

[30] Foreign Application Priority Data

Jun. 5, 1985 [AT] Austria .................................. 1704/85

[51] Int. Cl.[4] ........................................... G01N 23/10
[52] U.S. Cl. ........................................ 378/51; 378/53; 378/54
[58] Field of Search .............. 378/51, 52, 53, 54, 378/56, 66; 250/358.1, 359.1; 356/441, 442

[56] References Cited

U.S. PATENT DOCUMENTS

| 3,160,745 | 12/1964 | Foster | 378/51 |
| 3,449,567 | 6/1969 | Olivier et al. | 378/51 |
| 4,084,426 | 4/1978 | Gales . | |
| 4,539,649 | 9/1985 | Michaelis et al. | 378/53 |

FOREIGN PATENT DOCUMENTS

| 2907103 | 9/1980 | Fed. Rep. of Germany . | |
| 3138159 | 4/1983 | Fed. Rep. of Germany | 378/51 |
| 1112770 | 5/1968 | United Kingdom . | |
| 1225494 | 3/1971 | United Kingdom . | |
| 1240991 | 7/1971 | United Kingdom . | |
| 1264009 | 2/1972 | United Kingdom . | |
| 1327044 | 8/1973 | United Kingdom . | |
| 1533587 | 11/1978 | United Kingdom . | |
| 1533586 | 11/1978 | United Kingdom . | |
| 1575726 | 9/1980 | United Kingdom . | |

Primary Examiner—Janice A. Howell
Assistant Examiner—David P. Porta
Attorney, Agent, or Firm—Herbert Dubno

[57] ABSTRACT

Particle size analysis is carried out in a cuvette traversed by a plurality of vertically spaced light curtains which, because of the spacing, allows precision mesurements to be obtained without problems arising from the scanning of a sedimentation cell.

18 Claims, 8 Drawing Sheets

METHOD OF AND APPARATUS FOR GRAIN-SIZE ANALYSIS

FIELD OF THE INVENTION

Our present invention relates to a method of and an apparatus for grain-size or particle-size analysis of the distribution of a particulate in a liquid, utilizing the sedimentation principle and in which a concentration measurement is made by monitoring the attenuation of a wave-energy ray traversing the liquid containing the particulate to be measured, the wave energy being light, X-rays or the like.

BACKGROUND OF THE INVENTION

For a wide variety of technological processes, it is necessary to determine the grain-size distribution or particle size distribution of powders, e.g. a particulate having a grain size between 0.1 micrometer and 200 micrometers. One possible approach to such distribution measurements is to monitor the sedimentation process of the powder in a liquid since larger particles sediment more rapidly than smaller particles. This can be done, for example, by the method according to Andreas as set out in German Industrial Standards DIN 66 111 and DIN 66 115.

In this system, samples are taken at time intervals from the region of the bottom of the vessel in which the particles are caused to sediment from the liquid. The solids content of the particles can be used as a measurement of the particle diameter or the sieve size through which the particles could be expected to pass as calculated utilizing the additional parameters of particle density, liquid density, viscosity and fall height, and of course, time. A sedimentation balance operates under similar principles except that here the sedimentation particles are not drawn off by suction but are collected on the balance. The increase in weight with respect to time permits calculation of the grain size distribution.

The sedimentation process can be monitored, however, in another way. For example, it can be followed by an arrangement which includes a horizontal light beam or ray located in the vicinity of the bottom of the vessel above the body forming the bottom. With this arrangement, a measurement of the attenuation of the light beam by the suspended particles can be made. Initially the light attenuation by the suspended particles is comparatively great and after sedimentation of the larger particles, more light is permitted to traverse the cuvette to reach the sensor responding to the light transmission through the cuvette. From the change in attenuation with time, the particle size distribution can be calculated. An electrical light sedimentometer using these principles is described by O. Telle in V.D.I. Berichte, volume 7, 1955.

This system has, however, a significant disadvantage since the measurement takes a long time. If one wishes to ascertain with reasonable precision the large particle fraction of a suspension containing a wide variety size range, the cuvette must be so high that the larger particles or grains take from 5 to 20 seconds and even up to 30 seconds to sediment out, (see T. Allen, *Particle Size Measurement*, Chapman and Hall, London). If a shorter time span is used, this approach becomes inaccurate.

A tall cuvette of the time required for such fall times means that the fall times for the smallest particles can be up to 12 to 14 hours, making the entire process prohibitively long. To eliminate this disadvantage of an excessively long sedimentation time, devices have come on the market in which the measuring cuvette with the suspension is moved vertically from above downwardly relative to the light beam.

Hence the light beam initially traverses the cuvette in the region of the bottom thereof and toward the end of the process traverses the light beam in the vicinity of the upper surface. In this case, one need not await the migration of the smallest particles to the bottom of the cuvette.

The measuring process, depending upon the desired measurement particle size range, can be shortened to 15 to 30 minutes.

The reverse principles of operation can, of course, also be used, i.e. the light beam or, more specifically, the light "curtain" defined by the light source on one side of the cuvette, the light detector or sensor on the opposite side of the cuvette, and the ray passing between the source or emitter and the detector or sensor, can be moved along the cuvette upwardly.

Both of the principles just described do indeed avoid the drawback of prolonged measuring times, although they have significant disadvantages. As a result of the movement of the cuvette wall relative to the light beam, any optical characteristics of the wall that may differ from place to place therealong may introduce inaccuracies. These deviations in the optical properties of the wall can include wall thickness, refraction angle, parallelity of the wall surface of transparency. Additionally, relative movement causes wear which can contribute to inaccuracy and finally any actual movement of the cuvette can disturb the sedimentation process.

OBJECTS OF THE INVENTION

It is, therefore, the principal object of the present invention to provide an improved method of particle size distribution measurement and specifically analyzing the particulate distribution in suspension in a liquid which avoids the aforementioned drawbacks.

A more specific object of this invention is to provide a method of grain-size analysis of a particulate in suspension in which a particulate concentration measurement is made in a cuvette in which the particles are sedimenting and which allows the analysis to be made in a short time, with high accuracy and with a high degree of reproducibility.

It is also an object of this invention to provide an improved apparatus for carrying out a new method of analyzing the particle concentration sedimenting from a suspension.

SUMMARY OF THE INVENTION

These objects and others which will become apparent hereinafter are attained, in accordance with the invention by evaluating the attenuation of a multiplicity of horizontal light beams or rays, roentgen or X-rays, or more generally wave-energy rays which can be attenuated by the particles in suspension, which traverse, preferably simultaneously, the suspension or liquid at different levels.

In spite, therefore, of the attenuation measurements at each of a number of points along the height of the cuvette, rather than scanning the entire height of the cuvette over a measuring period, we are able to gain high precision since each measurement is taken concurrently with the other measurements at other heights under conditions which are identical from measurement to measurement so that any inhomogeneities in the cuvette walls and the like no longer affect the measurements.

In an apparatus for carrying out the invention, therefore, we have energy curtains which are provided at different levels and a multiplicity of these horizontal curtain arrangements are distributed over the height of the cuvette.

The term "light curtain" is used herein to mean the combination of a light source or emitter, the light ray or beam emitted from this source and the sensor which monitors the intensity of the beam on the other side of the cuvette from the source.

According to a feature of the invention, a single light source can be provided and each emitter for the particular light ray can derive from a mirror reflecting light from the common source.

It has been found to be advantageous for precision in measurement that the upper surface of the measurement volume be precisely and rapidly defined or established.

The apparatus can then include a spoon with a planar horizontal underside which can define the upper surface of the liquid and at the level of a gauge for this upper surface can have parallel to this underside a gap, notch or other through passage for a light ray.

Alternatively, setting of the liquid surface in the cuvette can be established by a cover provided with a diaphragm slit which is set into the cuvette.

The spoon can be provided with passages enabling the agitation or stirring of the suspension.

It has been found to be possible with a distance of 1.5 mm between the underside of the spoon and the uppermost light curtain to maintain the error of at most 0.15 mm or 10% in height determination. This may be acceptable considering the speed with which the determination can be made because the level can be readily established, the spoon being used to stir up the suspension first and then to establish the level of the upper surface without any delay in the latter stage or requirement for separate devices for stirring the suspension at the commencement of a measurement and for defining the upper surface of the measured volume. It is therefore an important aspect of the invention to provide in a method of grain size analysis of a particulate in a suspension in a liquid in which a particulate concentration measurement is made, the improvement which comprises the steps of:
 causing the particulate to sediment in a sample of the liquid;
 directing horizontal wave-energy rays through the sample at a plurality of different levels thereof; and
 ascertaining attenuation of intensity of the horizontal wave-energy rays caused by their traversal of the sample and the particulate therein to form the measurement.

The wave-energy rays can be light rays or X-rays. Stray wave energy of an uppermost one of the rays can be detected by at least one sensor.

The method can further comprise the step of standardizing for the attenuation of the wave-energy rays by passing the wave-energy rays through a corresponding sample containing a known particulate particle-size distribution in a standard suspension to form a reference value for the measurement.

The attenuation of the intensity of the horizontal wave-energy rays can be ascertained for each of the horizontal wave-energy rays by a respective sensor upon which the respective ray impinges, the sensors outputting respective signals representing the intensity of the respective ray, the method further comprising evaluating the signals to determine the attenuation by utilizing the signal from each sensor at a point in time at which the largest settling particle passing each sensor has the same falling velocity as the largest particle is detected at a time $t_m$ by the next-lower sensor.

At the beginning of a measurement the total concentration of the suspension can be detected and compared with predetermined limiting values of the concentration.

The rays can form respective light curtains which are monitored to determine uniformity of distribution of the particles in the suspension.

In another aspect of the invention, an apparatus for grain size analysis of a particulate in a suspension in a liquid in which a particulate concentration measurement is made, comprises:
 a cuvette having walls transparent to wave-energy rays and receiving the suspension and enabling the particulate to sediment in a sample of the suspension contained in the cuvette;
 means for directing horizontal wave-energy rays through the sample at a plurality of different levels thereof; and
 means forming respective horizontal wave-energy curtains with the means for directing the rays for ascertaining attenuation of intensity of the horizontal wave-energy rays caused by their traversal of the sample and the particulate therein to form the measurement, whereby the curtains are distributed over the height of the cuvette.

The light curtains can be spaced from an upper surface of the sample in the cuvette by distances given substantially by the formula:

$$h_n = \{h_1^{(N-n)} \cdot h_N^{(n-1)}\}^{(1/(n-1))}$$

wherein:
 N is the number of curtains over the height of the cuvette,
 n is curtain number counting from the bottom of the cuvette,
 $h_1, h_2, \ldots, h_n$ represent the distance of the curtain of the curtain number $1, 2, \ldots, n$, from the upper surface, and
 the deviation of $h_n$ from the value calculated from the formula is less than $(+/-0.2\ h_n)$, preferably at most $(+/-0.1\ h_n)$.

The cuvette can be formed by an upright light permeable tube standing on the bottom of a receptacle for the suspension. Advantageously a light-transmissible thermally insulating material separates the light source from the cuvette. Preferably the light-transmissible thermally insulating material is a thermally insulating glass plate.

The means for directing horizontal wave-energy rays through the sample at a plurality of different levels thereof can include a single source of the wave-energy rays and a multiplicity of mirrors reflecting the wave energy from the source into horizontal rays, and the means forming respective horizontal wave-energy curtains with the means for directing the rays for ascertaining attenuation of intensity of the horizontal wave-energy rays caused by their traversal of the sample and the particulate therein to form the measurement includes respective detectors for the wave energy receiving the rays from the mirrors.

BRIEF DESCRIPTION OF THE DRAWING

The above and other objects, features and advantages of the present invention will become more readily apparent from the following description, reference being made to the accompanying drawing in which.

SPECIFIC DESCRIPTION

The principles of the invention will be described in connection with FIGS. 1-6.

Figure 1:
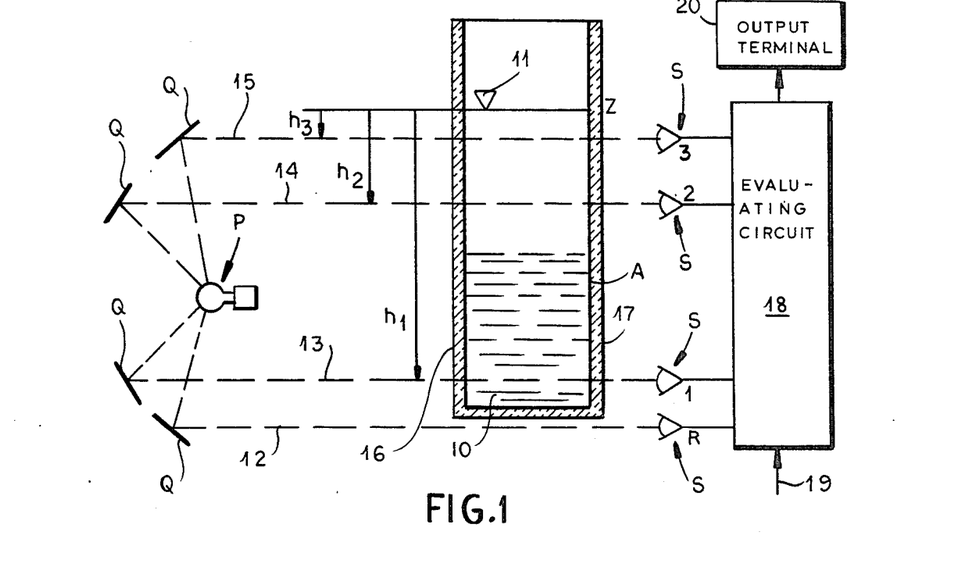
FIG. 1 is a diagram illustrating the method of the invention.
Figure 2:
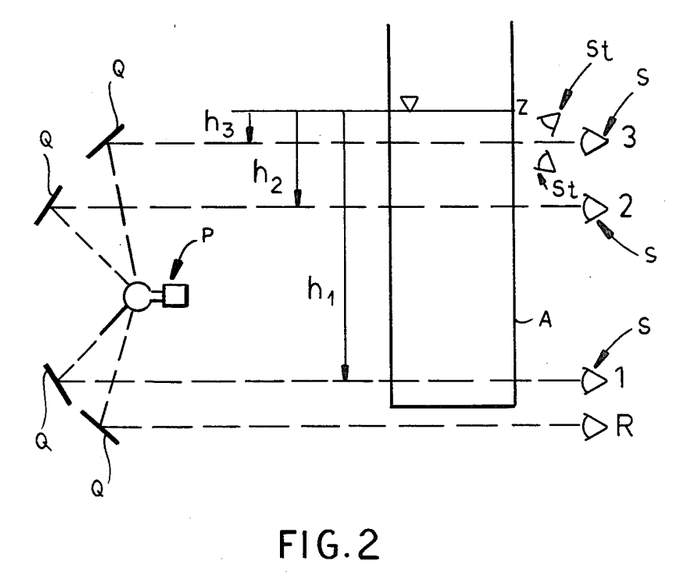
FIG. 2 is a diagram analogous to FIG. 1 of a system in which additional sensors are provided for stray light measurement.

As can be seen from FIGS. 1 and 2, the measuring cuvette A can contain a suspension generally represented at 10 whose upper surface is set at a level Z by a level or surface-establishing unit represented here at 11. R, 1, 2, 3 represent respective vertically spaced light curtains, each of which derives from a common light source P with which mirrors Q are juxtaposed to form the light rays 12, 13, 14, 15 ... each of which traverses the cuvette A which has light permeable walls 16, 17 and is intercepted by a respective sensor S. The sensors can work into a microprocessor based evaluation circuit 18 to which additional inputs required for calculation of the particle size distribution can be supplied at 19, the distribution being printed out or displayed on an output terminal 20.

In addition, the device can include stray light sensors $S_t$ outside the axis of the respective ray for at least the uppermost light curtain (FIG. 2), these stray light sensors detecting the stray light resulting from the Tyndall effect.

When the powder in suspension has a large proportion of fine particles (below 2 micrometers in particle size), the light scattering or stray light can have a significant effect on the measurement results since the small particles do not absorb the scattered light but deflect it to cause an attenuation of the rays which exceeds that which is due to interception by the surfaces of these particles. Such scattered or stray light can be fed to the evaluating circuit 18 to compensate for the light scattering. The use of stray light sensors for the light scattered by the fine particles broadens the measurement range in the fine particle direction. The scattered light measuring technique is of course described in the literature.

It will be understood, of course, that other wave-energy sources than light can be used to form the respective curtains, including, for example, roentgen or X-rays.

The sensors S of the light curtains 1, 2, 3 are measurement sensors while the sensor S of the light curtain R is a reference sensor with the output of which the signal of each measuring sensor is compared to compensate for deviations in the current supply or aging of the light source. The spacing of the light curtains from the sensors is selected so that the measuring ranges of the sensors adjoin one another as will be apparent from FIGS. 3 and 4.

Figure 3:
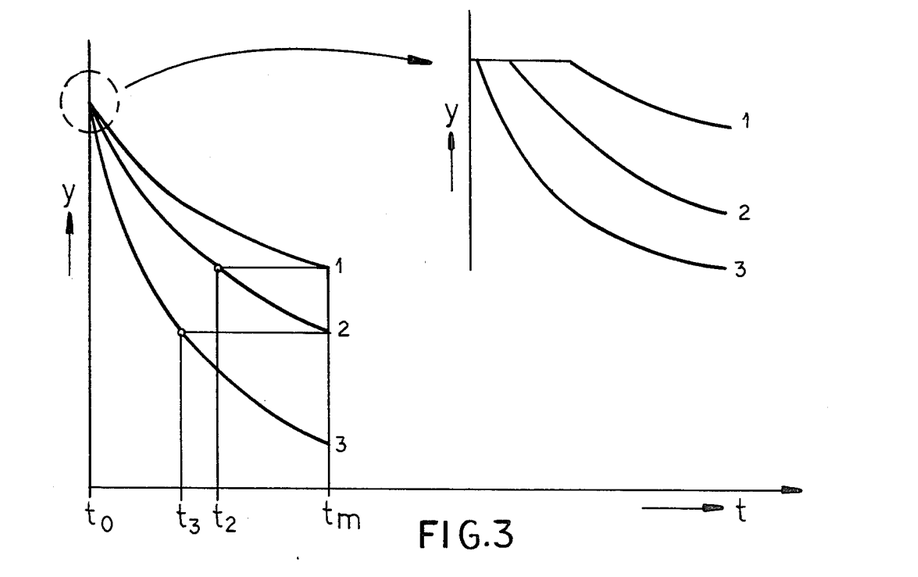
FIGS. 3-5 are graphs in which time is plotted along the abscissa while the ordinate represents detected light intensity so that the graphs show attenuation with time.

FIG. 3 shows the light attenuation Y of the three light curtains as a function of time. The light curtain 1 suffers the greatest attenuation at the end of the measuring period whereas the light curtain 3 which is closest to the upper surface suffers the least attenuation.

At the beginning of the measuring period, the sensor S of the light curtain 1 is predominantly unattenuated since the largest particles require a certain amount of time until they all have fallen into a position in which they can intercept the lowest light beam, i.e. have traversed the light curtain 1.

The signal of the sensor S of light curtain 3, however, shows a change immediately upon commencement of the measuring period since the largest particles begin to fall from the region of the upper surface almost immediately. Since at the commencement of the measuring period and over the brief initial part thereof the sedimentation has not stabilized, the initial signal is highly imprecise and is not evaluated by the circuit 18.

The greatest precision is obtained from the signals toward the end of the measuring interval and it is thus desirable to utilize the measuring interval back from the end of the measuring time $t_m$ to a point in time where the attenuation Y of the sensor S of the light curtain 2 at the time $t_m$ is equal to the attenuation of the light curtain 3, i.e. the point $t_3$. Thus the evaluation period can be the interval between $t_3$ and $t_m$. The signal from the sensor S of the light curtain 1 can be evaluated over the entire interval $t_o$ to $t_m$ thereby giving a determination as to the large particles which is at least as precise as those provided by other methods.

Based on the law of sedimentation of particles in a liquid, the signal curve for the light curtain 2 between $t_o$ and $t_2$ (FIG. 3) is identical with the curve of the sensor 1 when the time coordinate is multiplied by the ratio $h_i/h_2$. Similarly, the curve of the light curtain 3 between $t_o$ and $t_3$ is identical with that of the light curtain 2. The light curtains can thus be arranged optimally so that $t_2$ and $t_3$ are equal.

Optimum spacing between the light curtains is given in accordance with the invention by the formula:

$$h_n = h_1 \left( \frac{h_N}{h-1} \right)^{\frac{n-1}{N-1}} \tag{1}$$

wherein N is the number of light curtains, n is the number assigned to a particular light curtain counting from the bottom of the vessel, $h_1, h_2 \ldots h_n$ is the distance of the light curtains from the upper surface of the liquid (equal to the fall height of the particles).

This formula is based upon a number of considerations. The cuvette is traversed by a number N of light curtains. These are spaced by a distance $h_i (i=1, \ldots, N)$ from the upper edge of the measuring volume. The only question, then, is how the distance $h_i$ can be optimally chosen. This can be found from the formula (1) above. Each of the sensors supplies a signal representing light attenuation with time and after the major part of the large particle size fraction has sedimented, this attenuation becomes progressively less. This requires that all of the light curtains be located above the bottom body of the vessel.

Apart from the light attenuation which is the measurement of the concentration in the cross section of the cuvette at the level of the light curtain of the suspended particles, the sedimentation time can be determined automatically as the second important parameter from which the output in terms of the particle size distribution can be calculated.

The concentration of the powder in suspension is selected so that it is at most sufficiently high that the uppermost sensor for the light curtain provides a signal even at the end of the measuring period which is less than the upper limit prescribed by the German Industrial Standard DIN 66 111.

The selection of the measuring time requires consideration of a number of aspects:

1. Since at the beginning of the measurement the suspension is stirred or agitated and residual vortices or swirls may disturb the sedimentation process at the inception of the measurement operation, the first part of measured values is not evaluated. The vortices transport sedimented particles again to a higher level which can correspond to an error in the sedimentation time $t_u$.

To ensure maximum precision for all sensors, it is advantageous to have the waiting interval $t_i - t_o$ as long as possible and as much the same as possible for all sensors. The waiting time is thus defined as the time between the beginning of the measurement process of the initial utilization or evaluation of the signal from the sensor i.

2. The total measuring process should be as brief as possible so that the measuring process for all sensors should terminate simultaneously.

The height $h_i$ is selected so that all light curtains are simultaneously effective at the beginning of the measurement, terminate at the end of the measuring time and have output signals which are evaluatable during the intervening period.

As a rule the greatest height $h_1$ of the light curtain 1 can be given by the boundary conditions (largest particle diameter, viscosity of the liquid, maximum permissible physical height of the device, desired precision . . . ). In addition the smallest height $h_N$ of the uppermost light curtain can be given by the structural boundary conditions (smallest particle diameter, smallest possible slit width of uppermost diaphragm slit, reproducibility of the spoon setting).

There are also other criteria which must be considered:

The signal of the next highest light curtain $(n+1)$ can be evaluated from the point in time at which the largest directly falling particle equal to the largest particle at the end of the measuring time crosses the light curtain n. Since this is an identical particle at each case, the falling speed is equal.

The falling speed of a sedimenting particle, given in terms of an ideal ball-shaped particle with a diameter x in a viscous liquid at small Reynolds numbers is given by the relationship:

$$W_{S(x)} = \frac{x^2(\rho_S - \rho_L)}{18\eta}$$

Where $\rho_S$ is the density of the particle $\rho_L$ is the density of the liquid and $\eta$ is the dynamic viscosity of the liquid.

The falling viscosity of the particles detected by the last of the sensors n is given by $$W_s(n) = \frac{h_n}{t_m} \frac{h_n + 1}{t_{(n+1)}} \tag{A1}$$

With an optimum sensor arrangement, all the times $t_i$ (where i is greater than 1) are equal, namely, $t_w$. The last equation can thus be written:

$$t_w = t_{w(n+1)} = t_m \frac{h_{n+1}}{h_n} \tag{A2}$$

For the next higher sensor this means that:

$$t_w = t_{w(n+2)} = t_m \frac{h_{n+2}}{H_{n+1}} \tag{A3}$$

Substitution of equation A2 in equation A3 gives:

$$t_w = t_m \cdot \frac{h_{n+2}}{h_n \frac{t_w}{t_m}} \tag{A3'}$$

or $$\frac{t_w}{t_m} = \sqrt{\frac{h_{n+2}}{h_n}} \tag{A4}$$

Expanding this for N optimally arranged light curtains, one obtains:

$$\frac{t_w}{t_m} = \sqrt[N-1]{\frac{h_N}{h_1}} \tag{A5}$$

Since the optimal reversal time point for n optimally arranged sensors for a given measuring time at the smallest and greatest light curtain heights is known, the optimal height of the intervening light curtains $h_2 \ldots h_{N-1}$ can be calculated:

$$\frac{t_w}{t_m} = \sqrt[N-1]{\frac{h_N}{h_1}} = \frac{h_{n+1}}{h_n} \tag{G1 A6}$$

For $n=1$, $h_2$ is given by the relation:

$$h_2 = h_1 \left(\frac{h_N}{h_1}\right)^{\frac{1}{N-1}} \tag{G1 A7}$$

For $h_3$ this means:

$$h_3 = h_1 \left(\frac{h_N}{h_1}\right)^{\frac{2}{N-1}} \quad \text{(G1 A8)}$$

and generalizing one obtains:

$$h_n = h_1 \left(\frac{h_N}{h_1}\right)^{\frac{n-1}{N-1}} \quad \text{(G1 1)}$$

This can be reformulated simply as $$h_n = (h_1^{N-n} \cdot h_N^{n-1})^{\frac{1}{(n-1)}} \quad (1')$$

N can in principle be any whole number greater than 2.

In practice, N can equal 3 with highly effective results.

To evaluate the three sensor signals with the greatest precision, as described in connection with FIG. 3, one uses the curve portion over the longest usable measuring interval. In particular, the signal from the sensor S of the light curtain 1 can be used over the total measuring time. The light signal from the curtain 2 can be used from the time point $t_2$ at which a particle traverses this light curtain having fallen from the height $h_2$ corresponding to the measuring time for the light curtain 1 (see FIG. 3). The light curtain 3, of course, is effective over the time interval $t_3$ corresponding to the point at which the particle has fallen through the distance $h_3$ in the same period $t_m$ that the particle has fallen through the distance $h_2$.

The same applies for all further sensors.

Figure 5:
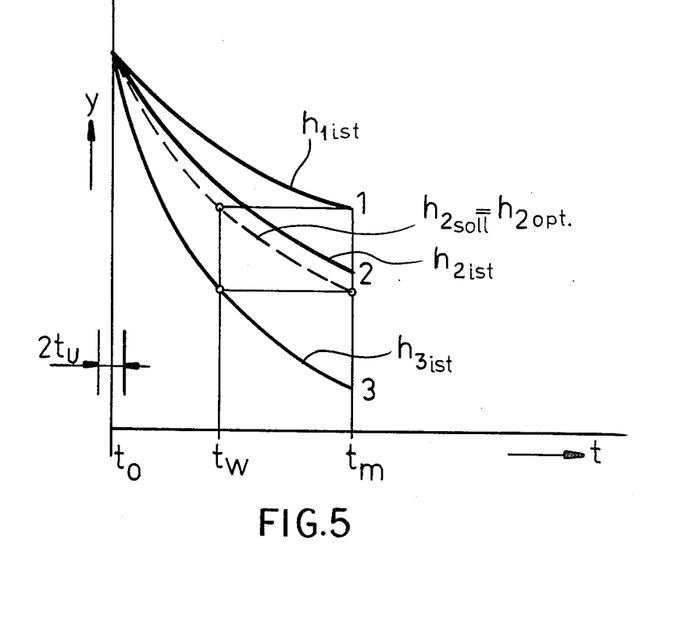

When the heights of the light curtains are selected in accordance with the above formulae, the times $t_2$, $t_3$ . . ., etc. are all equal and correspond to the time $t_w$ (see FIG. 5). The formula 2 then applies:

$$t_1 = t_2 \times h_1/h_2. \quad (2)$$

The same applies for sensor 3 and so forth.

Figure 4:
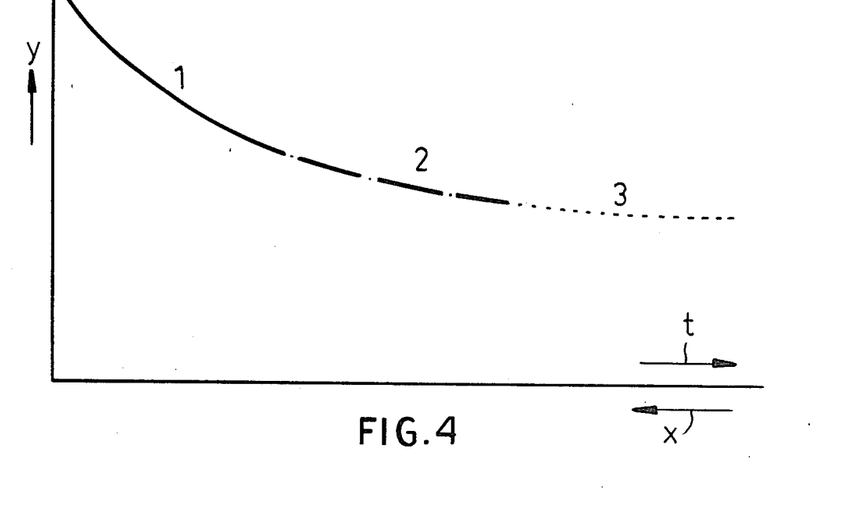

The signals from the light curtains 1, 2, 3 . . . can, as is apparent from FIG. 4, lie along a single curve where a time coordinate for the sensor 2, for example, is multiplied by the ratio $h_1/h_2$ in accordance with the equation:

$t_1 = t_2 \times h_1/h_2$. The same applies for sensor 3 and so forth.

Since the sedimentation time required for the particle to fall, for example from the level Z through the height $h_3$, a measure of the particle size X, the time axis in FIG. 4 can correspond to a particle size axis. The measurement of the particle size X is given by the sedimentation time t and the measurement for the concentration is given by the light attenuation Y.

The calculation of the concentration from the light attenuation is described by O. Telle (op. cit.). It is thus possible to determine for a given collection of particles the fraction with a given particle size in the particle collection, the particle size distribution as a whole and particle sizes from the light attenuation, sedimentation height and sedimentation time.

In practice, the height $h_i$ of the $i^{th}$ light curtain from the liquid level will deviate by the fabrication tolerances from the calculated height so that the signal of the sensor, for example the sensor 2, cannot optimally be used so that there may be a loss in precision. By optimal selection of the height $h_i$ of the $i^{th}$ light curtain, the waiting time (time between measurement commencement $t_o$ and the beginning of signal evaluation from the $i^{th}$ sensor or the i-1 sensor, and thus the time period $t_1 - t$, or $(t_i - 1) - t_o$) is shortened so that the actual evaluation commences only following elimination of the unreliability factor (see T. Allen, *Particle Size Measurement*, Chapman and Hall, London). In practice one can wait say 30 seconds after stirring of the suspension before the first measurement is taken.

As is also apparent from FIG. 3, the interval over which the measurement at the sensor S of light curtain 2 is taken can be equal to the interval between the point at which the attenuation is equal to the final attenuation of the sensor S of the light curtain 1 and the final attenuation at the end of the measuring period $t_m$ whereas the evaluation period for the sensor S of the light curtain 3 is equal to the duration from the point at which its attenuation is equal to the final attenuation of the sensor S of light curtain 2 to the end of the measuring period $t_m$.

FIG. 5 shows the results with a device using three light curtains 1, 2, 3 and in which the light curtain 2 is positioned at a location which can be considered too deep. The broken line represents the result when the light curtain 2 is optimally positioned.

In the optimum position, of course, $t_2$ coincides with $t_3$ and both are equal to $t_w$.

Since the actual measuring range of the light curtain 2 terminates prior to the set point measuring range of the broken line curve, the signal from the sensor 3 must be utilized earlier. This foreshortens the waiting time $t_3 - t_o$ (FIG. 5).

The error $$t_u / (t_3 - t_o)$$

is inversely proportional to the waiting time.

Since the waiting time is proportional to the height $h_i$, this should not be greater than 0.2 $h_i$ and preferably should not deviate more than 0.1 $h_i$ from the calculated value.

Standardization is required for numerous particle size measuring devices and other measuring devices using light scattering. With devices operating under the sedimentation principle, standardization is not customary. Where light is used for measurement, however, one customarily must provide a standardization since the optical characteristics of the powders varies widely and their special measurements are expensive and problematical. It is, therefore, far less expensive and advantageous to measure the powder with a device in accordance with a particular principle and then use this powder as a standardization powder. Naturally this principle can be applied to the present invention as well, i.e. once a measurement is made utilizing the invention on a powder, this powder can become a standard powder.

Naturally it is advantageous to use a standard powder, a powder with a known particle size distribution and one which will have a distribution as close as possible to that of unknown powders which will be measured.

The standardization process, of course, can be carried out in the same way as the measurement on the unknown.

Initially one determines whether the concentration of powder in the suspension is sufficient. When insufficient powder is supplied to the cuvette, the light attenuation is minimal and the electrical signal which is outputted by the sensors cannot be effectively evaluated. Measurements in the measuring range are relatively imprecise. When this situation arises, measurement can be interrupted.

Sedimentation of the particles can also be disturbed when the concentration is too high, a condition which can be referred to as "hindered settling", whereby the German Industrial Standards DIN 66 111, 66 115 and 66 116 have established maximum permissible concentration values for particle size measurements by sedimentation. Routinely one also, therefore, determines whether, after measurement has been initiated, the particle concentration exceeds the maximum permissible limit. The lower and upper limits for each powder can be determined empirically with no difficulty.

Assuming that the boundary limits have not been exceeded, the liquid level is established with precision by the so-called spoon. A precise liquid level is, of course, important since the time that it takes for a particle to fall from the liquid surface through each light curtain 1 . . . N is directly proportional to the distance, or "height" $h_i$ . . . $h_N$ by which the respective light curtain is lower than the level Z of the suspension surface. Any error in this height has an effect on the precision of the fall-time determination and, as a consequence on the grain size X.

This is especially significant for the uppermost sensor N whose height $H_N$ responds to the shortest fall time. With a measuring device as described and in accordance with the present invention, it is important that the liquid level Z be defined with complete reproducibility since this level is important for standardization as well as for successive measurements which are to be reproducible or directly comparable with the standardization.

Figure 6:
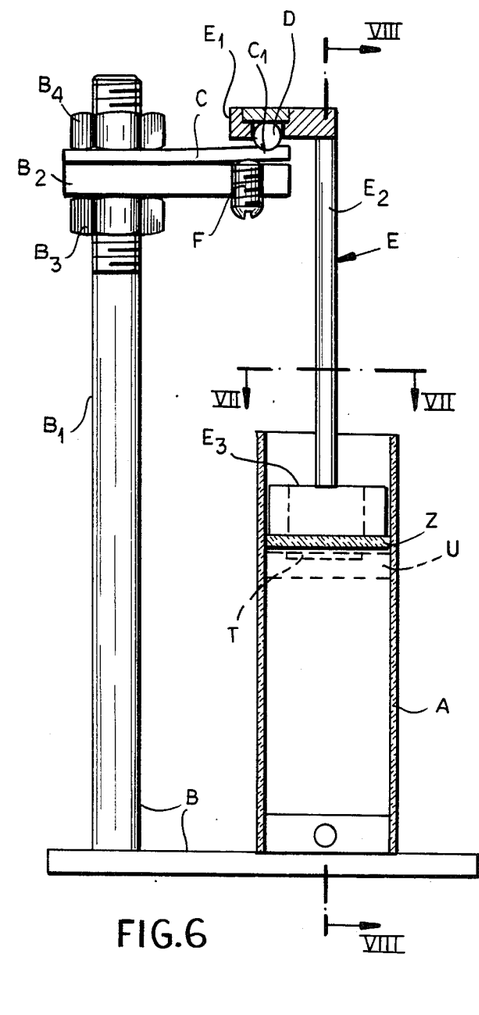
FIG. 6 is an elevational view partly in diagrammatic section illustrating a first embodiment of an apparatus for carrying out the invention.

One approach to precise establishment of the liquid level has been shown in FIG. 6. The cuvette A rests upon a rigid, strong and stiff support B which is provided with a threaded shaft $B_1$ on which a horizontal bar $B_2$ can be adjustably positioned between a pair of counternuts $B_3$, $B_4$.

Figure 8:
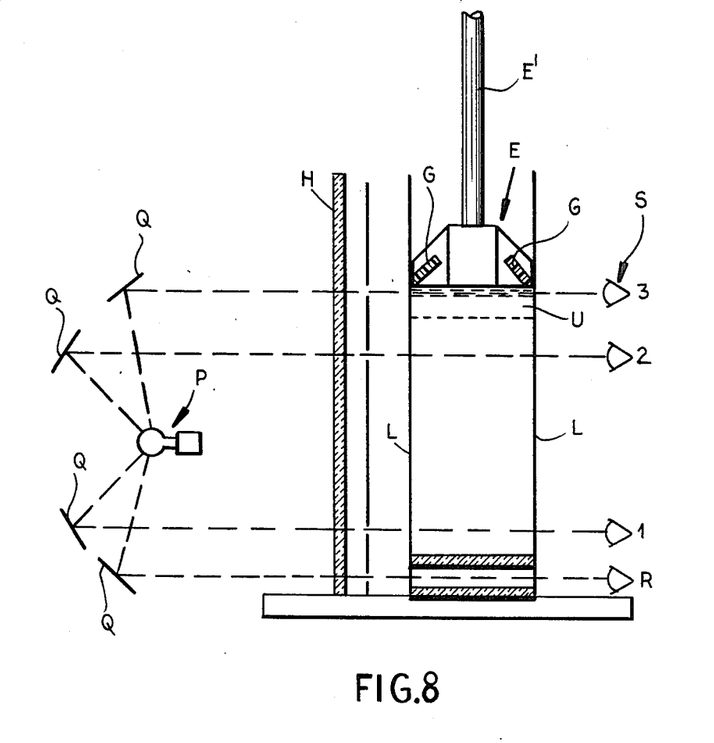
FIG. 8 is a vertical section taken along the line VIII—VIII of FIG. 6 but illustrating the array of sensors and the source which have not been shown in FIG. 6.

A resilient tongue C is clamped between the nut $B_4$ and the bar $B_2$ and can have a fine height adjustment at its free end in the form of a screw F threaded into the bar $B_2$ and supporting a ball D of a hard material (e.g. chromium-alloy steel, glass, silicon carbide). The spoon E is formed with an end piece $E_1$ receiving the ball D which rests in a recess $C_1$ of the tongue C. The shank E of the spoon is formed at its lower end with a block $E_3$ whose underside can define the fluid level Z. As can be seen from FIG. 8, the underside of the spoon can be formed with a gauge U having a gap T. The suspension of the spoon by the ball D centers the spoon and ensures precise reproducibility of a particular level.

With the aid of the adjusting screw F, the height of the tongue C and thus of the spoon is adjusted until the uppermost light curtain has the greatest intensity and this height is then fixed by the screw.

The spoon is provided with two side edges G of synthetic resin material which can wipe against the windows formed by opposite walls of the cuvette. The underside of the spoon is as planar and horizontal as possible so that a consant fall height $H_N$ for all particles is ensured.

Figure 7:
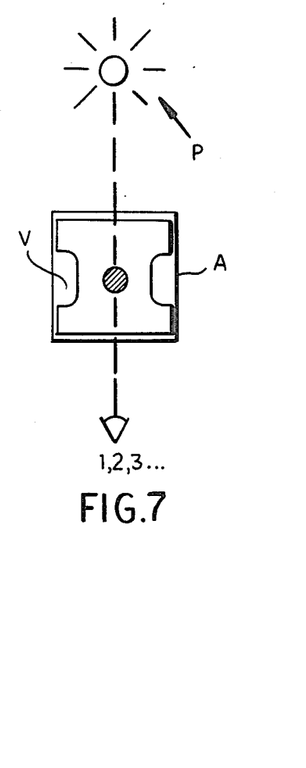
FIG. 7 is a diagrammatic plan view of a cuvette into which a spoon for establishing the upper surface level of the liquid has been introduced and corresponds to a view taken along the line VII—VII of FIG. 6.

On the two sides parallel to the light rays, the spoon is provided with cutouts through which the suspension can flow past the spoon upon raising and lowering of the spoon. The flow past of the particles during measurement does not affect the measurement since cutouts V, as can be seen in plan view, lie outside the paths of the light curtains.

A stirring and homogenization of the suspension can be effected by raising and lowering the spoon and of course the shank of the spoon and thus be greater than the height of the cuvette.

As with all particle measuring processes, a representative sample of the total collective must be taken. For the method of the invention, the sample can amount to several tenths of a gram and preferably is prepared as described in German Industrial Standards DIN 66 111 and 66 115.

The cuvette is filled with the pure suspension liquid and is inserted in the device. Particles in the cuvette are stirred up in the liquid by raising and lowering the spoon. The spoon is then suspended from the ball as data acquisition is effected by introducing the COMMAND TEST to the evaluation circuit. This of course starts the test.

The light attenuation of the individual light curtains 1, 2, 3 . . . N and the reference light curtain R, i.e. the signals $S_{1T}$. . . $S_{NT}$, $S_{RT}$ are measured and stored, 1 . . . NR designating the respective light curtains and T signifying that the signal is obtained from the pure suspension liquid, i.e. a blank.

If the signal values $S_{1T}$. . . $S_{NT}$ vary with time, that signifies that the liquid contains particles with diameters in the measurement range, i.e. the liquid is contaminated. In this case, the blank measurement is carried out for at least as long as the later actual measurements will require.

If the light amplitude at the sensors does not vary with time or the measured values lie within predetermined limits, corresponding to a reliable grain-suspension liquid, the test sampling of the liquid can be interrupted and the data aquisition records the intensity of the light signal as that resulting from the "pure" suspension liquid.

The particle samples are then introduced into the "pure" suspension liquid. The sample masses are calculated according to German Industrial Standards DIN 66 111, 66 115. After stirring with the spoon and suspending the latter on the ball, the following tests are made:

Concentration of the suspension: With insufficient concentration, the light attenuation is insufficient and at excessive concentrations the particles hinder sedimentation of one another. By comparison of the light attenuation between two predetermined limits, it is possible to determine whether the concentration is in the correct range. A report is provided on the display if it is not.

Uniform distribution of the suspension:

By comparison of the light attenuation at the three sensors, it can be seen whether the suspension has been agitated sufficiently since the attenuation should be initially equal. If this is not the case, the agitation can begin again. When the concentration is unsatisfactory or the stirring is not sufficient, this fact is indicated to the data processor and is registered on the display or output terminal 20. If after both of these tests the variation is within the permissible limits, the test is continued with measurement by registration of the sensor signals and storing the latter.

Depending upon the desired precision and the smallest particle diameter to be ascertained, the measurement period can be increased or decreased. A longer measurement time, of course, allows greater accuracy and the measurement of smaller particles.

The relationship between measuring time and the smallest measurable particle diameter can be calculated in accordance with Stokes law as so shown for the calculation of the optimal height arrangement previously.

Before further evaluation, however, the sensor signals are tested for plausibility.

Periodic or intermittent variations in lamp brightness are eliminated by forming the differences of the individual sensor signals $S_1 \ldots S_N$ with the signal $S_R$ from the reference sensor. These differences in the measurements are then used to form differential signals representing the attenuation in accordance with the following relationships:

$$V_1 = (S_1 - S_R) - (S_{1T} - S_{RT}) \quad (4)$$

$$V_N = (S_N - S_R) - (S_{NT} - S_{RT})$$

V thus represents the difference between each sample data and the suspension liquid data.

The light attenuation $V_1 \ldots V_N$ is then divided by the attenuation at time $T_O$ to give normalized measurement values standardized to unity:

$$\frac{V_1}{V_{1(t=o)}} = M_1 \quad (5)$$

$$\frac{V_2}{V_{2(t=o)}} = M_2$$

This yields dimensionless values $M_1 \ldots M_N$ for the respective sensors.

In a similar way the standardization factors $L_1 \ldots L_N$ are obtained, the value $L_1$ for the standard powder corresponding to the measured value $M_1$ of the unknown sample.

Multiplication of each value $M_1 \ldots M_N$ with the corresponding standard factor $L_1 \ldots L_N$ yields the frequency factor $Q_1, Q_2, Q_3 \ldots$ in dependence upon the periodic size which is used for standardization.

$$Q_r = M_r \cdot L_r \quad (6)$$

$$r = 1, 2, 3$$

The provision of a plurality of light curtains in stepped heights in accordance with equation 1 can be accomplished in various ways, the only problem being the exact reproduction of the spacing $h_N$ between the liquid surface Z and the uppermost light curtain. This distance $h_N$ should be held as small as possible so that the smallest particles can be evaluated in the shortest measuring time.

Figure 9:
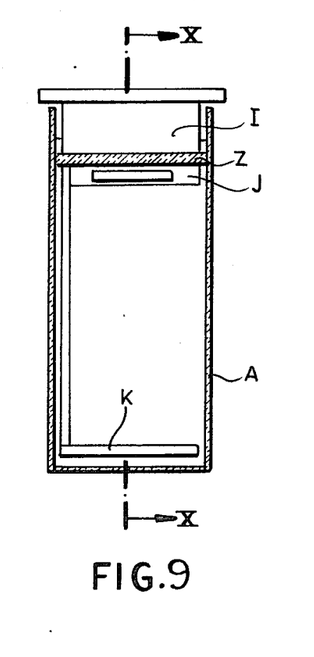
FIG. 9 is a vertical section through a second embodiment of the apparatus of the invention.
Figure 10:
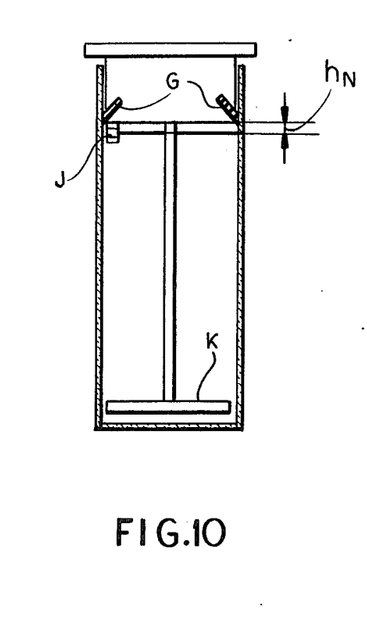
FIG. 10 is a section along the line X—X of FIG. 9, both FIGS. 9 and 10 being highly diagrammatic in form.

In the embodiment of FIG. 9, the cuvette A has a cover 1 having a closure edge G like the spoon previously described. On the underside of the plug forming the cover I is a rib J in which a diaphragm slit is milled to be traversed by the uppermost light curtain. The height $h_N$ is thereby fixed by the plug. The underside of the plug should preferably be horizontal and to agitate the suspension, the plug may be attached to an agitating spoon or stirrer K.

The various heights $h_1, h_2 \ldots$ of the light curtains can be established by a fixed diaphragm outside the sample volume and of course the plug I, instead of resting on the cuvette can be supported by a shank and suspended as has been shown in FIG. 6.

Figure 11:
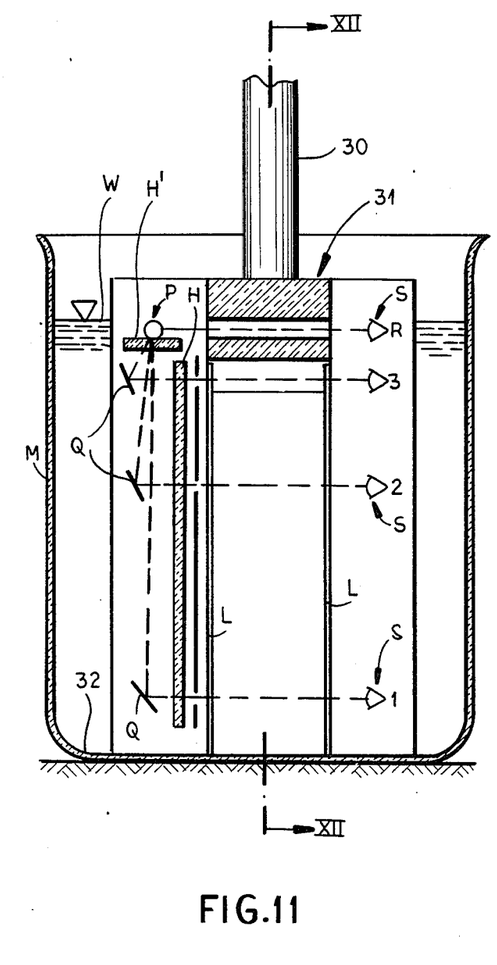
FIG. 11 is a vertical section through a third embodiment of the invention also in highly diagrammatic form.
Figure 12:
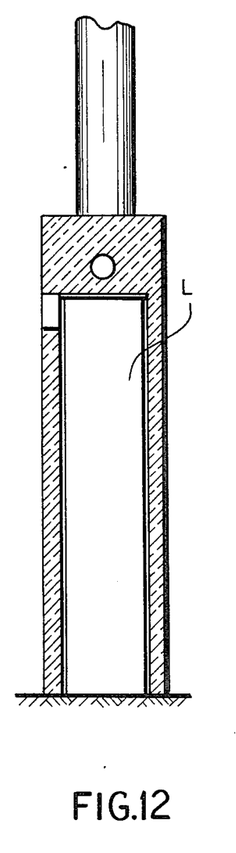
FIG. 12 is a section taken along the line XII—XII of FIG. 11.

Still another embodiment has been illustrated in FIGS. 11 and 12 in the form of an immersion unit. Here the light source, the deflecting mirrors, sensors and cuvettes are formed into a unitary measuring head. The cuvette does not have a bottom and instead is provided with a slit at the level of the liquid surface W in the outer vessel M.

The entire measuring head 31 is carried by a rod 30 with the aid of which it can be immersed in the suspension to rest on the bottom 32 of the vessel M. The rod 30 also can be tubular to supply the current for the light source as well as the conductors running from the sensors to the evaluating circuit. Once the head is rested upon the bottom of the vessel M, the measurement or standardization process can be carried out.

It is important in all of the embodiments described to avoid heating the cuvette with the lamp supplying the light rays. A thermally insulating glass plate H advantageously can be provided to prevent excessive radiant or convective heating of the cuvette. In the embodiment of FIG. 11, the heat-insulating glass plate is located between the mirrors and the cuvette while another heat-insulating glass plate H' can be disposed horizontally between the lamp and the mirrors. Any heating of the cuvette, of course, results in falsification of the measurement.

Figure 13:
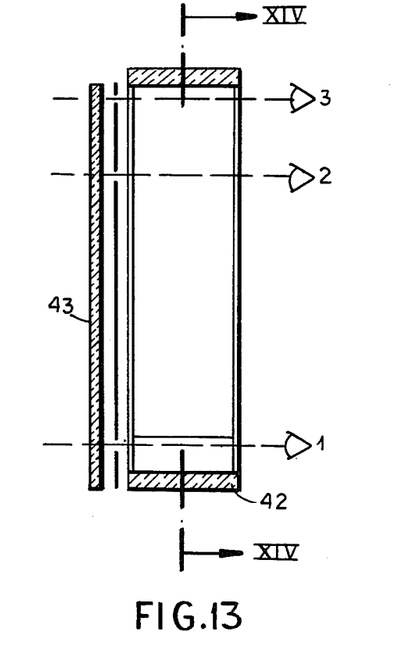
FIG. 13 is a vertical section through a fourth embodiment of the invention.
Figure 14:
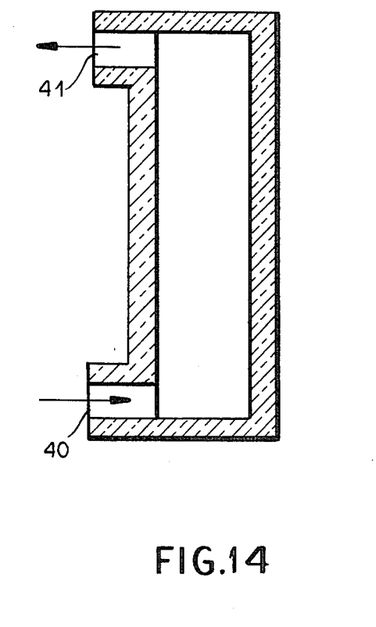
FIG. 14 is a section taken along the line XIV—XIV of FIG. 13.

The cuvette of FIGS. 13 and 14 is closed on all sides but is provided on one side perpendicular to the planes of the surfaces traversed by the light curtains with an inlet 40 and an outlet 41 through which the suspension can be fed. In this case, the unit forms a flow cell.

Figure 15:
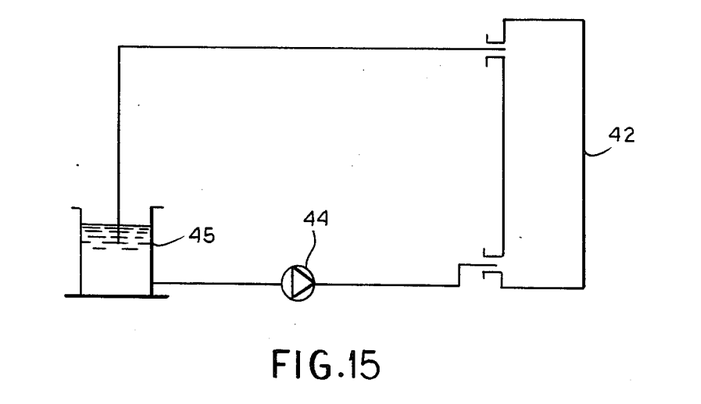
FIG. 15 is a diagram of a machining device utilizing the cuvette or cell of FIGS. 13 and 14.

The advantage of a precisely defined upper surface, of course, confronts the disadvantage of cleaning difficulties. This is especially the case where the apparatus is connected in a processor, for example a crystallizer. When, however, the unit is used as a flow cell (see FIG. 15), this problem is avoided.

In FIGS. 13 and 14, therefore, the cuvette 42, shielded from heat by the insulating plate 43 and provided with the light curtains 1, 2, 3, can be connected to a pump 44 circulating the suspension from an external vessel 45.

We claim:

1. In a method of grain size analysis of a particulate in a suspension in a liquid in which a particulate concentration measurement is made, the improvement which comprises the steps of:

causing said particulate to sediment in a sample of said liquid in a stationary container;

directing at least three horizontal nonscanning wave-energy rays through said sample from respective fixed sources at respective different fixed and spaced apart levels thereof such that a distance between an uppermost ray and the next lower ray is less than the distance between said next lower ray and a said ray therebelow;

ascertaining attenuation of intensity of said horizontal wave-energy rays caused by their traversal of said sample and the particulate therein to form said measurement, the attenuation of the intensity of said horizontal wave-energy rays being ascertained for each of said horizontal wave-energy rays by a respective sensor upon which the respective ray impinges, said sensors outputting respective signals representing the intensity of the respective ray; and evaluating said signals to determine the attenuation by utilizing the signal from each sensor at a point in time at which the largest settling particle passing each sensor has the same falling velocity as the largest particle is detected at a measurement time $t_m$ by the next-lower sensor.

2. The improvement defined in claim 7 wherein said wave-energy rays are light rays.

3. The improvement defined in claim 7 wherein said wave-energy rays are x-rays.

4. The improvement defined in claim 7 wherein stray wave energy of an uppermost one of said rays is detected by at least one sensor.

5. The improvement defined in claim 7, further comprising the step of standardizing for the attenuation of said wave-energy rays by passing said wave-energy rays through a corresponding sample containing a known particulate particle-size distribution in a standard suspension to form a reference value for said measurement.

6. The improvement defined in claim 1 where in said rays form respective light curtains which are monitored to determine uniformity of distribuion of said particles in said suspension.

7. In a method of grain size analysis of a particulate in a suspension in a liquid in which a particulate concentration measurement is made, the improvement which comprises the steps of:

causing said particulate to sediment in a sample of said liquid;

directing horizontal wave-energy rays through said sample at a plurality of different levels thereof; and ascertaining attenuation of intensity of said horizontal wave-energy rays caused by their traversal of said sample and the particulate therein to form said measurement, at the beginning of a measurement the total concentration of the suspension being detected and compared with predetermined limiting values of said concentration.

8. In an apparatus for grain size analysis of a particulate in a suspension in a liquid in which a particulate concentration measurement is made, the improvement which comprises:

a cuvette having walls transparent to wave-energy rays and receiving said suspension and enabling said particulate to sediment in a sample of said suspension contained in said cuvette;

means for directing at least three horizontal nonscanning wave-energy rays from respective vertically fixed sources through said sample at a plurality of different levels thereof while said sample is held fixed; and means forming respective horizontal wave-energy curtains with said means for directing said rays for ascertaining attenuation of intensity of said horizontal wave-energy rays caused by their traversal of said sample and the particulate therein to form said measurement, said curtains being light curtains, said light curtains being spaced from an upper surface of the sample in said cuvette by distances given substantially by the formula:

$$h_n = \{h_1^{(N-n)} \cdot h_N^{(n-1)}\}^{(1/(n-1))}$$

wherein:

N is the number of curtains over the height of the cuvette, n is curtain number counting from the bottom of the cuvette, $h_1, h_2, \ldots, h_n$ represent the distance of the curtain of the curtain number $1, 2, \ldots, n$, from said upper surface, and the deviation of $h_n$ from the value calculated from the formula is less than $(+/-0.2\ h_n)$.

9. The improvement defined in claim 8 wherein said deviation is at most $(+/-0.1\ h_n)$.

10. The improvement defined in claim 8 wherein said means for directing said rays includes at least one x-ray source.

11. The improvement defined in claim 8, further comprising means for establishing a precise position of said upper surface in said cuvette and including a spoon having a planar horizontal underside defining said upper surface and formed with a through going gap parallel to said underside and traversed by one of said rays.

12. The improvement defined in claim 8, further comprising means for establishing a precise position of said upper surface said cuvette and including a cover formed with a diaphragm slit.

13. The improvement defined in claim 8 wherein said spoon is provided with at least one passage enabling the agitation of said suspension.

14. The improvement defined in claim 8 wherein said cuvette is formed by an upright light permeable tube standing on the bottom of a receptacle for said suspension.

15. The improvement defined in claim 8 further comprising light-transmissible thermally insulating material separating said curtains from said cuvette.

16. The improvement defined in claim 15 wherein said light-transmissible thermally insulating material is a thermally insulating glass plate.

17. In an apparatus for grain size analysis of a particulate in a suspension in a liquid in which a particulate concentration measurement is made, the improvement which comprises:

a cuvette having walls transparent to wave-energy rays and receiving said suspension and enabling said particulate to sediment in a sample of said suspension contained in said cuvette;

means for directing at least three horizontal nonscanning wave-energy rays from respective vertically fixed sources through said sample at a plurality of different levels thereof while said sample is held fixed; and means forming respective horizontal wave-energy curtains with said means for directing said rays for ascertaining attenuation of intensity of said horizontal wave-energy rays caused by their traversal of said sample and the particulate therein to form said measurement, said means for directing horizontal wave-energy rays through said sample at a plurality of different levels thereof including a single source of said wave-energy rays and a multiplicity of mirrors reflecting said wave energy from said source into horizontal rays, and said means forming respective horizontal wave-energy curtains with said means for directing said rays for ascertaining attenuation of intensity of said horizontal wave-energy rays caused by their traversal of said sample and the particulate therein to form said measurement includes respective detectors for said wave energy receiving said rays from said mirrors.

18. The improvement defined in claim 17, further comprising light-transmissible thermally insulating material separating said mirrors from said cuvette.

* * * * *